United States Patent [19]
Calvani et al.

[11] Patent Number: 5,955,424
[45] Date of Patent: Sep. 21, 1999

[54] USE OF L-CARNITINE AND ITS ALKANOYL DERIVATIVES FOR REDUCING THE TOXIC EFFECTS OF CYCLOSPORIN-A AND OTHER IMMUNOSUPPRESSANT DRUGS

[75] Inventors: Menotti Calvani; Luigi Mosconi, both of Rome, Italy

[73] Assignee: Sigma-Tau Industrie Farmaceutiche Riunite S.p.A., Rome, Italy

[21] Appl. No.: 08/580,993

[22] Filed: Jan. 3, 1996

[30] Foreign Application Priority Data

Jan. 20, 1995 [IT] Italy .................................. RM95A0037

[51] Int. Cl.$^6$ .......................... A61K 38/00; A61K 31/205
[52] U.S. Cl. ................................................ 514/11; 514/556
[58] Field of Search ........................................ 514/556, 11

[56] References Cited

PUBLICATIONS

Wanner et al, Metabolism, "Serum Carnitine Levels and Carnitine Esters of Patients after Kidney Transplantation: Role of Immunosuppression", vol., 37, No. 3, (Mar., 1988) pp. 263–267.

*Primary Examiner*—Jerome D. Goldberg
*Attorney, Agent, or Firm*—Oblon, Spivak, McClelland, Maier & Neustadt, P.C.

[57] ABSTRACT

The use of L-carnitine or of an alkanoyl L-carnitine or their pharmacologically acceptable salts is described for producing a medicament for inhibiting nephrotoxicity and vasculotoxicity resulting from the administration of an immunosuppressant drug such as cyclosporin-A, tacrolimus, rapamicine and deoxyspergualine.

7 Claims, No Drawings

USE OF L-CARNITINE AND ITS ALKANOYL DERIVATIVES FOR REDUCING THE TOXIC EFFECTS OF CYCLOSPORIN-A AND OTHER IMMUNOSUPPRESSANT DRUGS

The present invention relates to a novel use of L-carnitine and some of its alkanoyl derivatives for reducing the toxic effects resulting from the administration of cyclosporin-A and other immunosuppressants possessing nephrotoxic and vasculotoxic activity.

More specifically, the invention relates to the coordinated use of L-carnitine or an alkanoyl L-carnitine or the pharmacologically acceptable salts thereof, wherein by "coordinated use" of the aforesaid compounds it is meant indifferently either the co-administration, i.e. the substantially concomitant supplementation of L-carnitine or acyl L-carnitine or a pharmacologically acceptable salt thereof and the immunosuppressant, as active ingredients, or the administration of a combination preparation containing a mixture of the aforesaid active ingredients, in addition to suitable excipients, if any.

Alkanoyl L-carnitines wherein the alkanoyl group has 2–6 carbon atoms, such as acetyl, propionyl, butyryl, valeryl and isovaleryl, are preferred. Propionyl L-carnitine is particularly preferred. Also the pharmacologically acceptable salts of L-carnitine and the aforesaid carnitine derivatives can be used.

Pharmaceutically acceptable salts of L-carnitine or alkanoyl L-carnitine include, in addition to the inner salts, all pharmaceutically acceptable salts which are prepared by the addition of acid to L-carnitine or alkanoyl L-carnitine, respectively, and which do not give rise to undesirable toxic or collateral effects. The formation of pharmaceutically acceptable acid addition salts is well known in the pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

The aforesaid novel protective activity of L-carnitine and derivatives thereof, particularly propionyl L-carnitine, was found to be carried on, in addition to cyclosporin-A, also towards further nephrotoxic and vasculotoxic immunosuppressants such as tacrolimus, rapamicine, ascomicine, deoxyspergualine and derivatives and congeners thereof.

L-carnitine and the aforesaid derivatives thereof can be administered as various pharmaceutical compositions, either alone or in combination with excipients, adjuvants and the like, which facilitate their administration and absorption.

Alternatively, L-carnitine or its derivatives can be compounded with the immunosuppressants.

The resulting pharmaceutical compositions (tablets, capsules, granules, vials, infusion bottles, etc) can be administered either orally or parenterally.

Organic salts, glucose, inorganic phosphates, aminoacids, vitamins and the like can be added as auxiliary ingredients to the orally or parenterally administrable compositions of the present invention.

Previous therapeutical uses of L-carnitine are already known.

For instance, L-carnitine has been used in the cardiovascular field in the treatment of acute and chronic myocardial ischaemia, angina pectoris, cardiac arrhythmias and insufficiency. In nephrology, L-carnitine has been administered to chronic uraemic patients who are subject to regular haemodialysis treatment with a view to counteracting muscular asthenia and the onset of muscular cramps.

Further therapeutical uses are the restoration of HDL/LDL+VLDL ratio to normal and in total parenteral nutrition.

Also therapeutic uses of acetyl L-carnitine are already known in the therapeutic treatment of ischemia and myocardial arrhythmias, functional peripheral vascular diseases of the arteries, such as Raynaud's disease and acrocyanosis and the treatment of subjects affected by altered cerebral metabolism which is found for example in senile and pre-senile dementia and in Alzheimer's disease.

Also propionyl L-carnitine is known to lend itself to the therapeutical treatment of cardiovascular disorders and peripheral vascular diseases.

However there is no correlation between the previously known therapeutic uses of carnitine and its derivatives and that which forms the subject of this invention.

Hypertension and arterial disease are phenomena which often accompany the administration of cyclosporin A and which, at the kidney level, take the form of an impairment of kidney function (Klintmaln G. B. G., Iwatsuk G., Stazel T. R., Lancet 2, 470, 1981).

The nephrotoxicity induced by cyclosporin A appears, in fact, to be the result of a general arterial disease which is associated with tubular atrophy and glomerular ischaemia (Jackson N. M., Humes H. D., J. Pharm. Exp. Ther., 242, 749, 1987).

The consequent reduced kidney function is therefore a highly limiting factor for the administration of cyclosporin A at high doses and for prolonged periods of time such as are necessary to obtain the immuno-suppressive effect required in many therapies in which cyclosporin A is administered, as in organ transplants, rheumatoid arthritis, psoriasis, diabetes mellitus and many other immunologically based diseases.

A similar vasculotoxic and nephrotoxic action limiting their therapeutic use is also exerted by other immunosuppressive drugs such as tacrolimus (also known as FK-506), rapamicin, deoxyspergualine and their analogues and derivatives (Fung Y. Y., Alessiani M., Aba-Elmad K., Transplant Proc., 23, 105, 1991; McCanley Y., Fung Y. Y., Starzel T. E., Transplant Proc., 23, 3143, 1991; Calne R. Y., Collier J., Lim S., Lancet 2, 227, 1989: Ochiai T. J., Isono K., Transplantation 56, 15, 1989; Suzuki S., Ann. N.Y. Acad. Sci. 696, 263, 1993; Amemija H., Ann. N.Y. Acad. Sci. 685, 196, 1993).

Despite the fact that cyclosporin A is a polypeptide and, to be precise, a cyclopeptide metabolite of fungi such as Toypocladium inflatium and Trichoderma polyporum (Kahan B. D. Ed. Cyclosporine. Grunne and Sfratton, Orlando, 1983; Dreyfuss M. H., Hoffman H., Ritai Europ. J. Appl. Microbiol. 3, 125, 1976), whereas tacrolimus and rapamicin are macrolides isolated from Streptomyces tsukubaensis (Kimo T. et Coll., J. Antibiot. 40, 1249, 1987) and Streptomyces hygroscopicus (Vezina C. A., Kudelski A., Schjol N., Antibiot. 28, 721, 1975), respectively, just as ascomycin is a macrolide (Aroi T., J: Antibiot. 15, 110, 1962), their molecular structure presents conformational similarities which explain why they have a similar mechanism of action as regards above all their ability to bind to similar intracellular protein structures such as the cyclophyllines and calcineurine on which the immunosuppressive response is based. This similar mechanism of action may also explain the similarity observed in the occurrence of secondary toxic effects, particularly at vascular and renal level which these drugs are capable of inducing.

Reducing the nephrotoxic effects of cyclosporin and other equally vasculotoxic immunosuppressive drugs therefore appears to be very important in order to be able to fully exploit the therapeutic properties of these substances or to prolong treatment with them so as to achieve a complete therapeutic effect.

It has now been found that carnitine and its above-mentioned derivatives—particularly propionyl L-carnitine—are capable of reducing the nephro-toxicity of cyclosporin A as of other equally vasculotoxic immuno-suppressive drugs, such as tacrolimus and analogues in such a way as to make it possible to use them therapeutically even at high doses and for lengthy periods of time without having to discontinue their administration owing to the occurrence of their well known dangerous toxic side effects, particularly those of a nephrotoxic type.

Indicated here below are a number of the pharmacological tests performed which show that the administration of L-carnitine and its derivatives, particularly propionyl L-carnitine, is suitable for reducing, almost to the point of abolishing, the toxic effects of cyclosporin A, tacrolimus and other similar immunosuppressive drugs, which are especially marked at kidney level.

EXPERIMENTAL TESTS

Tests on the inhibition of toxic endothelial factors induced by immuno-suppressants.

A substantial body of experimental results exists to show that cyclosporin A is capable of releasing various factors responsible for its hypertensive and nephrotoxic effect from the endothelia, including endothelin and histamine (Kon V., Suguira M., Imagami T., Hoover R., Kidney Int. 37, 1487, 1990).

The experiments performed indicate that the administration of L-carnitine or propionyl L-carnitine is capable of inhibiting or abolishing the release of these substances responsible for cyclosporin A toxicity.

These results were obtained in a group of experiments performed on perfused rat kidney using increasing doses of cyclosporin A (1, 2, 4, 8 mg/l) and assessing, on the reflux fluid, the amount of histamine and endothelin released by the renal tissue.

L-carnitine, acetyl L-carnitine and propionyl L-carnitine were injected, each at two different doses (2 mg/l and 5 mg/l), before cyclosporin A, and the histamine and endothelin-1 released were then re-measured on the renal reflux fluid collected using a fluorimetric method and RIA, respectively.

From the ratio between the amounts of histamine and endothelin-1 released by cyclosporin A alone and after prophylactic treatment with the carnitines, it emerges that the reduction in histamine and endothelin-1 release induced by this prophylactic treatment is very significant. The most marked reduction is the one obtainable with administration of propionyl L-carnitine (above 59 and 68% reductions of histamine and endothelin, respectively), thus demonstrating that important factors responsible for cyclosporin nephrotoxicity can be inhibited by the carnitines, and particularly by propionyl L-carnitine.

We give a number of examples of the experiments performed and the results obtained.

CARNITINE-INDUCED PROTECTION AGAINST HISTAMINE AND ENDOTHELIN-1 RELEASE ON ISOLATED KIDNEY PERFUSED WITH CYCLOSPORIN A (2 mg/l)

| | % Inhibition of release (*) | |
|---|---|---|
| Carnitines | Histamine | Endothelin-1 |
| L-carnitine (2 mg/l) | 15.8 ± 1.1 | 6.2 ± 0.6 |
| L-carnitine (5 mg/l) | 29.2 ± 2.1 | 28.8 ± 1.6 |

-continued

CARNITINE-INDUCED PROTECTION AGAINST HISTAMINE AND ENDOTHELIN-1 RELEASE ON ISOLATED KIDNEY PERFUSED WITH CYCLOSPORIN A (2 mg/l)

| | % Inhibition of release (*) | |
|---|---|---|
| Carnitines | Histamine | Endothelin-1 |
| Acetyl L-carnitine (2 mg/l) | 12.2 ± 0.8 | 24.6 ± 2.1 |
| Acetyl L-carnitine (5 mg/l) | 18.6 ± 0.6 | 35.4 ± 3.1 |
| Propionyl L-carnitine (2 mg/l) | 47.4 ± 3.2 | 45.4 ± 2.8 |
| Propionyl L-carnitine (5 mg/l) | 59.2 ± 3.6 | 68.8 ± 5.2 |

(*) values after 1-min perfusion

Similar favourable results were obtained by assessment of the release of histamine and endothelin-1 from perfused isolated kidney using tacrolimus instead of cyclosporin A.

In this case, too, the carnitine inhibition of the tacrolimus-induced release of both histamine and endothelin-1 is above 45% and 60%, respectively.

CARNITINE-INDUCED PROTECTION AGAINST HISTAMINE AND ENDOTHELIN-1 RELEASE ON ISOLATED RAT KIDNEY PERFUSED WITH TACROLIMUS (400 mcg/l)

| | % Inhibition of release | |
|---|---|---|
| Carnitines | Histamine | Endothelin-1 |
| L-carnitine (2 mg/l) | 12.4 ± 0.9 | 7.2 ± 0.8 |
| L-carnitine (5 mg/l) | 18.6 ± 1.3 | 20.6 ± 1.1 |
| Acetyl L-carnitine (2 mg/l) | 10.5 ± 1.5 | 16.6 ± 2.4 |
| Acetyl L-carnitine (5 mg/l) | 19.9 ± 0.8 | 24.5 ± 1.9 |
| Propionyl L-carnitine (2 mg/l) | 37.2 ± 2.9 | 35.8 ± 3.3 |
| Propionyl L-carnitine (5 mg/l) | 44.8 ± 3.6 | 60.4 ± 4.2 |

Test on inhibition of toxic effects of immunosuppressants on renal tubule enzymes One of the well documented effects of the renal toxicity induced by cyclosporin A and by the other vasculotoxic immunosuppressants is that they cause renal tubule lesions that can be assessed by assay of enzyme markers such as alanine-aminopeptidase (AAP) and N-acetyl-glucosaminidase (NAG).

In a series of experiments performed on isolated rat kidney perfused with cyclosporin A (2 mg/l) or with tacrolimus a substantial release of both AAP and NAG was, in fact, detectable, thus indicating substantial tubular damage. By contrast, prophylactic administration of carnitine, particularly propionyl L-carnitine, reduced the occurrence of these toxic signs by more than 50% (percentage reduction in AAP release as a result of propionyl L-carnitine administration [5 mg/l] more than 50% and in NAG release more than 55% in the case of cyclosporin A perfusion, as against more than 50 and more than 58%, respectively, in the case of tacrolimus perfusion.

CARNITINE PROTECTION AGAINST RENAL TUBULE DAMAGE INDUCED BY TACROLIMUS (400 mcg/l) AS ASSESSED BY ASSAY OF THE ENZYMES ALANINE-AMINOPEPTIDASE (AAP) AND N-ACETYL-GLUCOSAMINIDASE (NAG)

| | % Inhibition of release | |
|---|---|---|
| Carnitines | AAP | NAG |
| L-carnitine (2 mg/l) | 16.2 ± 0.3 | 13.7 ± 0.9 |
| L-carnitine (5 mg/l) | 21.2 ± 1.1 | 27.2 ± 2.2 |
| Acetyl L-carnitine (2 mg/l) | 15.7 ± 2.1 | 15.4 ± 0.6 |

-continued

CARNITINE PROTECTION AGAINST RENAL TUBULE
DAMAGE INDUCED BY TACROLIMUS (400 mcg/l) AS
ASSESSED BY ASSAY OF THE ENZYMES ALANINE-
AMINOPEPTIDASE (AAP) AND N-ACETYL-
GLUCOSAMINIDASE (NAG)

| | % Inhibition of release | |
|---|---|---|
| Carnitines | AAP | NAG |
| Acetyl L-carnitine (5 mg/l) | 28.8 ± 1.9 | 25.7 ± 1.7 |
| Propionyl L-carnitine (2 mg/l) | 36.7 ± 2.6 | 31.6 ± 2.8 |
| Propionyl L-carnitine (5 mg/l) | 51.5 ± 3.4 | 58.7 ± 4.1 |

CARNITINE PROTECTION AGAINST RENAL TUBULE
DAMAGE INDUCED BY CYCLOSPORIN A (2 mg/l) AS
ASSESSED BY ASSAY OF THE ENZYMES ALANINE-
AMINOPEPTIDASE (AAP) AND N-ACETYL-
GLUCOSAMINIDASE (NAG)

| | % Inhibition of release (*) | |
|---|---|---|
| Carnitines | AAP | NAG |
| L-carnitine (2 mg/l) | 22.4 ± 1.9 | 19.4 ± 1.5 |
| L-carnitine (5 mg/l) | 30.2 ± 2.6 | 31.2 ± 2.8 |
| Acetyl L-carnitine (2 mg/l) | 18.6 ± 0.8 | 16.4 ± 1.2 |
| Acetyl L-carnitine (5 mg/l) | 18.4 ± 1.1 | 24.6 ± 1.8 |
| Propionyl L-carnitine (2 mg/l) | 42.8 ± 3.1 | 38.6 ± 2.4 |
| Propionyl L-carnitine (5 mg/l) | 55.8 ± 3.8 | 51.4 ± 4.2 |

(*) values after 5-min perfusion

Tests on carnitine inhibition of renal hypertensive effect induced by immunosuppressants The renal hypertension caused by cyclosporin A is due mainly to vasoconstriction of the glomerular arterioles and is another of the nephrotoxic effects caused by cyclosporin-A. In our experiments we observed that the administration of carnitines, and particularly of propionyl L-carnitine, is also capable of significantly inhibiting this cyclosporin-induced toxic effect. The evidence of this protective effect of carnitines was obtained using perfused rat kidney and measuring blood pressure by means of a manometer attached to the renal artery. By means of these tests it proved possible to demonstrate that the prophylactic administration of L-carnitine, and particularly of propionyl L-carnitine, significantly reduces the high blood pressure values induced by cyclosporin (2 mg/l). The percentage reduction caused by the administration of propionyl L-carnitine (2 mg/l) is approximately 20% as against approximately 60% with 5 mg/l of propionyl L-carnitine. The same doses of propionyl L-carnitine induce reductions of 28 and 36%, respectively, in the hypertension induced by 400 mcg/l of tacrolimus.

PROTECTIVE EFFECT OF CARNITINES ON RENAL
HYPERTENSION INDUCED BY CYCLOSPORIN A (2 mg/l)

| | % Inhibition of hypertensive effect | |
|---|---|---|
| Carnitines | 5 min | 20 min |
| L-carnitine (2 mg/l) | 5.2 ± 0.8 | 4.1 ± 1.5 |
| L-carnitine (5 mg/l) | 22.7 ± 2.8 | 20.5 ± 1.9 |
| Acetyl L-carnitine (2 mg/l) | 12.4 ± 1.5 | 10.1 ± 0.9 |
| Acetyl L-carnitine (5 mg/l) | 18.4 ± 1.7 | 22.4 ± 1.8 |
| Propionyl L-carnitine (2 mg/l) | 20.8 ± 2.1 | 18.8 ± 2.1 |
| Propionyl L-carnitine (5 mg/l) | 32.4 ± 2.6 | 44.6 ± 3.8 |

PROTECTIVE EFFECT OF CARNITINES ON RENAL
HYPERTENSION INDUCED BY TACROLIMUS (400 mcg/l)

| | % Inhibition of hypertensive effect | |
|---|---|---|
| Carnitines | 5 min | 20 min |
| L-carnitine (2 mg/l) | 6.4 ± 0.6 | 5.6 ± 1.7 |
| L-carnitine (5 mg/l) | 28.8 ± 2.1 | 21.2 ± 1.7 |
| Acetyl L-carnitine (2 mg/l) | 16.2 ± 1.4 | 11.4 ± 0.8 |
| Acetyl L-carnitine (5 mg/l) | 20.1 ± 1.8 | 14.8 ± 1.2 |
| Propionyl L-carnitine (2 mg/l) | 24.6 ± 1.9 | 25.2 ± 1.8 |
| Propionyl L-carnitine (5 mg/l) | 28.7 ± 2.2 | 36.2 ± 2.1 |

Morphometric assessment of the protective effect of carnitines against cyclosporin-A-induced nephrotoxicty Also using the morphometric method on kidney sections fixed in formalin and stained with haematoxylin-eosin and measuring the ratio of the capillary tuft to the Bowman capsule (CD/BD ratio) at the glomerular level and the ratio of the internal diameter to the basal membrane (ID/ED ratio) by means of a micrometer fitted to an optical microscope, it can be seen that the reduction in the CD/BD ratio and the increase in the ID/ED ratio, both indices of reduced kidney function such as that induced by cyclosporin-A in the isolated rat kidney, can be brought back to normal by the prophylactic administration of L-carnitine and, particularly, propionyl L-carnitine.

PROTECTIVE EFFECT OF CARNITINES ON GLOMERULAR
AND TUBULAR MORPHOMETRIC ALTERATIONS INDUCED
BY CYCLOSPORIN A

| | Morphometric indices | |
|---|---|---|
| | glomerular CD/BD | tubular ID/ED |
| Control | 0.96 ± 0.008 | 0.36 ± 0.02 |
| Cyclosporin (2 mg/l) | 0.75 ± 0.01 | 0.72 ± 0.07 |
| L-carnitine (2 mg/l) | 0.79 ± 0.004 | 0.55 ± 0.07 |
| L-carnitine (5 mg/l) | 0.81 ± 0.009 | 0.44 ± 0.009 |
| Acetyl L-carnitine (2 mg/l) | 0.76 ± 0.006 | 0.61 ± 0.04 |
| Acetyl L-carnitine (5 mg/l) | 0.78 ± 0.01 | 0.51 ± 0.003 |
| Propionyl L-carnitine (2 mg/l) | 0.85 ± 0.009 | 0.31 ± 0.004 |
| Propionyl L-carnitine (5 mg/l) | 0.89 ± 0.01 | 0.39 ± 0.003 |

We claim:

1. A therapeutical method for inhibiting nephrotoxicity and vasculotoxicity induced by administration of Cyclosporin A, which comprises orally or parenterally administering to a patient in need thereof a composition comprising an effective amount of both of of Cyclosporin A and an alkanoyl L-carnitine selected from the group consisting of propionyl, butyryl, valeryl and isovaleryl L-carnitine, or a pharmaceutically acceptable salt thereof, and a pharmacologically acceptable excipient.

2. The therapeutical method of claim 1, wherein the pharmacologically acceptable salt of said alkanoyl L-carnitine is selected from the group consisting of chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

3. The therapeutical method of claim 1, wherein said alkanoyl L-carnitine is propionyl L-carnitine.

4. A therapeutical method of inhibiting nephrotoxicity and vasculotoxicity induced by administration of Cyclosporin A, which comprises orally or parenterally administering to a patient in need thereof an effective amount of both Cyclosporin A and an alkanoyl L-carnitine selected from the group consisting of propionyl, butyryl, valeryl and isovaleryl L-carnitine, or a pharmaceutically acceptable salt thereof.

5. The therapeutical method of claim 4, wherein said immunosuppressant and said alkanoyl L-carnitine are administered concomitantly.

6. The therapeutical method of claim 4, wherein the pharmacologically acceptable salt of said alkanoyl L-carnitine is selected from the group consisting of chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

7. The therapeutical method of claim 4, wherein said alkanoyl L-carnitine is propionyl L-carnitine.

* * * * *